(12) United States Patent
Bono et al.

(10) Patent No.: US 12,262,898 B2
(45) Date of Patent: Apr. 1, 2025

(54) POWERED SURGICAL TOOL WITH TRANSMISSION

(71) Applicant: GLOBUS MEDICAL, INC., Audubon, PA (US)

(72) Inventors: Peter L. Bono, Bingham Farms, MI (US); James D. Lark, Troy, MI (US); Marshal Eric Finley, Birmingham, MI (US); Corey Freimark, Grand Haven, MI (US)

(73) Assignee: Globus Medical, Inc., Audubon, PA (US)

( * ) Notice: Subject to any disclaimer, the term of this patent is extended or adjusted under 35 U.S.C. 154(b) by 408 days.

(21) Appl. No.: 17/893,789

(22) Filed: Aug. 23, 2022

(65) Prior Publication Data

US 2023/0065982 A1   Mar. 2, 2023

Related U.S. Application Data

(60) Provisional application No. 63/273,115, filed on Oct. 28, 2021, provisional application No. 63/239,698, filed on Sep. 1, 2021.

(51) Int. Cl.
*A61B 17/16* (2006.01)
*A61B 17/88* (2006.01)
*A61B 17/00* (2006.01)

(52) U.S. Cl.
CPC ...... *A61B 17/1624* (2013.01); *A61B 17/1626* (2013.01); *A61B 17/1628* (2013.01); *A61B 17/1631* (2013.01); *A61B 17/8875* (2013.01); *A61B 2017/00141* (2013.01); *A61B 2017/00154* (2013.01); *A61B 2017/00398* (2013.01); *A61B 2017/00477* (2013.01)

(58) Field of Classification Search
CPC . A61B 17/16; A61B 17/1622; A61B 17/1624; A61B 17/1626; A61B 17/1628; A61B 17/1631; A61B 17/1671; A61B 17/32002; A61B 17/320748; A61B 17/072; A61B 17/07207; A61B 17/8875; A61B 2017/07214; A61B 2017/00473; A61B 2017/00477; A61B 2017/00398; A61B 2017/00141; A61B 2017/00154
USPC ...... 173/48, 216, 217, 213, 47, 109; 227/19, 227/175.1; 600/409, 424; 606/80, 130
See application file for complete search history.

(56) References Cited

U.S. PATENT DOCUMENTS

| | | | | |
|---|---|---|---|---|
| 6,721,986 | B2 * | 4/2004 | Zhuan | A61C 17/3418 74/25 |
| 8,943,634 | B2 * | 2/2015 | Sokol | A61C 17/26 15/22.1 |
| 9,539,043 | B2 * | 1/2017 | DeFalco | A61B 17/8875 |
| 9,826,989 | B2 * | 11/2017 | Chu | A61B 17/1624 |
| 10,194,922 | B2 * | 2/2019 | Bono | A61B 17/1671 |
| 10,835,263 | B2 * | 11/2020 | Bono | A61B 17/1628 |

(Continued)

*Primary Examiner* — Scott A Smith

(57) ABSTRACT

An oscillating drive mechanism for a surgical tool includes a motor having a rotor, a crank assembly hub, a link secured to the crank assembly hub, a pivot shaft, a shuttle including an arcuate rack gear secured to the link so that rotation of the crank assembly hub provides reciprocating rotary motion to the arcuate rack gear about the pivot shaft. A gear is meshed with the arcuate rack gear and is secured to an output shaft, whereby rotational motion of the motor induces rotary oscillating motion to the output shaft.

15 Claims, 11 Drawing Sheets

(56) References Cited

U.S. PATENT DOCUMENTS

| | | | |
|---|---|---|---|
| 11,000,306 B2* | 5/2021 | Bono | A61B 17/1671 |
| 11,147,579 B2* | 10/2021 | Edwards | A61B 17/32002 |
| 11,357,529 B2* | 6/2022 | Bono | A61B 17/320758 |
| 2007/0282344 A1* | 12/2007 | Yedlicka | A61B 17/1671 606/80 |
| 2013/0304069 A1 | 11/2013 | Bono et al. | |
| 2014/0275955 A1* | 9/2014 | Crawford | A61B 34/74 600/409 |
| 2018/0140307 A1* | 5/2018 | Bono | A61B 17/1628 |
| 2019/0117249 A1 | 4/2019 | Bono et al. | |
| 2020/0170660 A1 | 6/2020 | Bono et al. | |
| 2023/0067104 A1* | 3/2023 | Bono | A61B 17/1631 |

\* cited by examiner

POWERED SURGICAL TOOL WITH TRANSMISSION

PRIORITY CLAIM

The present application claims priority to U.S. Provisional Patent Application No. 63/273,115, filed Oct. 28, 2021, and U.S. Provisional Patent Application No. 63/239,698, filed Sep. 1, 2021, all of which are incorporated herein by reference.

FIELD OF THE INVENTION

The present invention relates to a rotary handheld surgical tool usable for cutting, drilling, and grinding.

BACKGROUND OF THE INVENTION

Powered rotary tools for surgery are well known in the art. Many surgeons consider them indispensable for certain surgical procedures, such as drilling, cutting, and grinding, particularly for orthopedic surgical procedures. They are used to modify tissue, such as bone, at the surgical site so that the surgical procedure can be effected. Such a tool typically includes a tool head, or end effector, that is rotated by an externally powered motor, such as an electrical motor. The tool head is part of an elongate shaft that is operably coupled to the rotor of the motor. The rotor of the motor effects rotation of the tool head and its shaft. The rotating tool head is used to effect some surgical operation, for example drilling, cutting, and grinding. An actuator is provided to selectively effect powering of the motor rotor to effect rotation of the effector.

Such tools are expensive and, because of the numerous parts, difficult and expensive to sterilize for reuse, often requiring partial or complete disassembly. Also, the tools have separable parts, such as the tissue modifying tool head. Besides removing tissue, such powered tools are used for other surgical steps, such as installing fasteners, such as screws. If a tool cannot be readily sterilized, it is disposed of after use, adding to the cost of surgery. Thus, when separate powered tools are used, multiple tools need to be sterilized or disposed of.

The prior art has provided surgical tools having a rotary cutter adapted to modify tissue, such as bone, cartilage, and discs, in a patient. Such tools, though, present a problem if the cutter encounters fibrous tissue such as muscle and nerves. Such fibrous tissue can wrap around the cutter and be damaged thereby. The prior art has also provided oscillating rotary tools for such surgical procedures, but the mechanisms used to effect oscillation of the cutter during rotation do not operate smoothly due to the mechanisms used to effect oscillation. An advance in such oscillating tools is represented by our co-pending applications: U.S. Non-Provisional patent application Ser. No. 13/469,665, entitled "Rotary Oscillating Bone, Cartilage, and Disk Removal Tool Assembly, filed May 11, 2012; and now issued U.S. Pat. No. 10,194,922, issued on Feb. 5, 2019; U.S. International Application No. PCT/US2013/037071, entitled "Rotary Oscillating Bone, Cartilage, and Disk Removal Tool Assembly", filed Apr. 18, 2013; U.S. Non-Provisional patent application Ser. No. 13/647,101, entitled "Cutting Tool for Bone, Cartilage, and Disk Removal", filed Oct. 8, 2012, and now issued U.S. Pat. No. 9,232,953, issued on Jan. 12, 2016; U.S. International Application No. PCT/US2013/063182, entitled "Cutting Tool for Bone, Cartilage, and Disk Removal", filed Oct. 3, 2013; U.S. Provisional Patent Application No. 62/460,481, entitled "Surgical Rotary Tool", filed Feb. 17, 2017, U.S. Non-Provisional patent application Ser. No. 15/895,352, entitled "Surgical Rotary Tool", filed Feb. 13, 2018; and U.S. Non-Provisional patent application Ser. No. 15/932,361, entitled "Surgical Rotary Tool", filed Feb. 16, 2018; U.S. Provisional Patent Application No. 62/423,624, entitled "Rotary Oscillating Surgical Tool", filed Nov. 17, 2016, and U.S. Non-Provisional patent application Ser. No. 15/814,891, entitled "Rotary Oscillating Surgical Tool", filed Nov. 16, 2017; U.S. Provisional Patent Application No. 62/423,651, entitled "Robotic Surgical System", filed Nov. 17, 2016; U.S. Provisional Patent Application No. 62/423,677, entitled "Robotic Surgical System", filed Nov. 17, 2016, and U.S. Non-Provisional patent application Ser. No. 15/816,861, entitled "Robotic Surgical System", filed Nov. 17, 2017.

Such tools are typically small and lightweight, with little room for drive mechanisms. They tend to operate at high cutting speeds for cutting efficiency and control by a surgeon. Oscillations are on the order of at least about 10,000 oscillations per minute (5,000 orbits per minute) and may be as high as 30,000-50,000 oscillations per minute or more. An oscillation is movement of the tissue modification device, such as a cutter, from one rotational position extreme to its other rotational extreme. The cutter configuration and material being removed will determine tissue modification device operating speed. Because of the high speed and need for precision placement and cutting, the tools need to be smooth in operation with little vibration.

SUMMARY OF THE DISCLOSURE

The present invention relates to a powered surgical tool that selectively rotates a tool head (effector) to effect tissue modification during a surgical procedure, and allows for use also as a fastener driver by a simple change of end effectors and shifting a drive selector.

Accordingly, it is desirable to provide a rotary surgical tool that has an output shaft that permits interchanging end effectors from a tissue modification device to a fastener driver.

It is further desirable to provide such a rotary surgical tool with a transmission that allows for shifting from high speed tissue modification driving mode to slow speed high torque fastener driving of the output shaft.

It is still further desirable to provide such a surgical tool that allows for selection of driving rotation of the output shaft for fastener driving.

It is still further desirable to provide an oscillating mechanism with high efficiency, low heat generation and high reliability.

Other objectives and advantages of this invention will become apparent from the following description taken in conjunction with any accompanying drawings wherein are set forth, by way of illustration and example, certain embodiments of this invention. Any drawings contained herein constitute a part of this specification, include exemplary embodiments of the present invention, and illustrate various objects and features thereof.

DESCRIPTION OF THE PRIOR ART

Examples of such rotary tools include those disclosed in U.S. Pat. Nos. 4,646,738; 5,735,535; 7,066,940; and U.S. Publication 2014/0246047. U.S. Pat. No. 4,646,738 is an electric motor powered tool that is quite complex, and it would require disassembly after use for sterilization. U.S.

Pat. No. 5,735,535 is an electric motor powered tool that is also complex, would require disassembly after use for sterilization, and uses a chuck to hold the tool head. U.S. Pat. No. 7,066,940 is also an electrically powered tool that, like the two previously mentioned tools, is complex, requires disassembly for sterilization, and has a separable cutting tool head. U.S. Patent Application Publication 2014/0246047 illustrates a different type of powered surgical tool, but it is not structured for using a rotary cutting tool. Like the aforementioned tools, it would require disassembly for sterilization and is quite complex in structure.

Even though advancements have been made over the years, no one has provided a simpler surgical tool that provides an advance in the art of rotary surgical tools that simplifies their use and provides for both tissue modification and screw installation functions in a single powered tool.

DETAILED DESCRIPTION OF THE INVENTION

Figure 1:
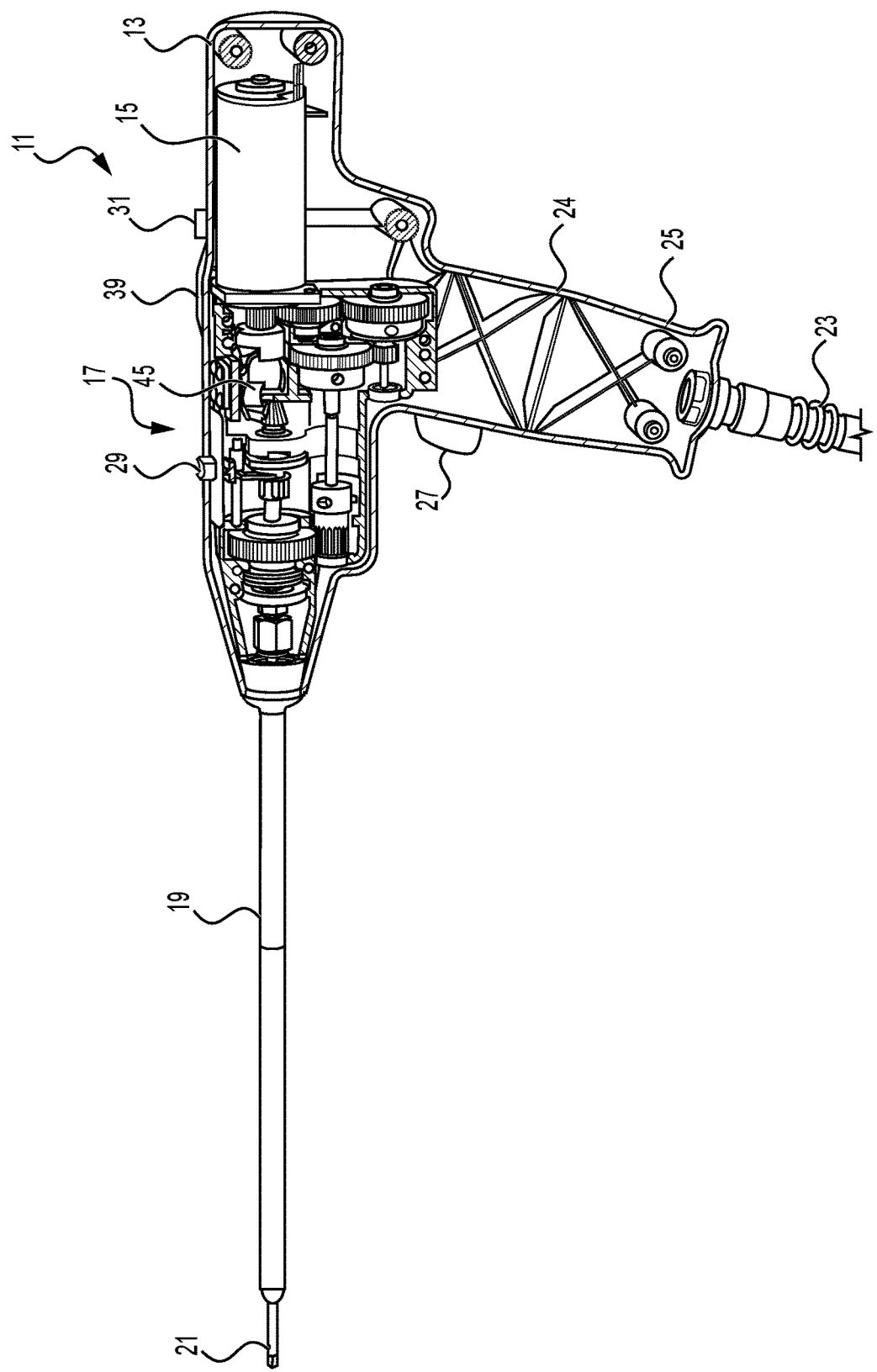
FIG. 1 is an isometric view of a surgical tool usable for tissue modification and fastener driving with a portion broken away to show internal details.

Referring to FIG. 1, the reference numeral 11 designates generally a power operated surgical tool having an external housing 13 adapted to enclose and support various internal components, such as a motor 15 operably connected to a transmission, designated generally 17, which operably couples the motor 15 to an output shaft 19 that carries a tool coupler 21. In a preferred embodiment, the motor 15 is an electric motor that is operably coupled to a power source, as for example by a power cord 23. The housing 13 can be provided with a depending handle 24 for gripping by a surgeon for control of the surgical tool 11. The housing 13 can be formed of a polymeric (often referred to as plastic) material and can be formed by molding. Preferably, the housing 13 is formed by combining two halves that are suitably secured together by fasteners 25. Various controls accessible by the surgeon are provided for selecting operation modes of the tool 11 and can include an on-off power switch 27, a transmission operation mode selector 29, and a reversing switch 31.

Figure 2:
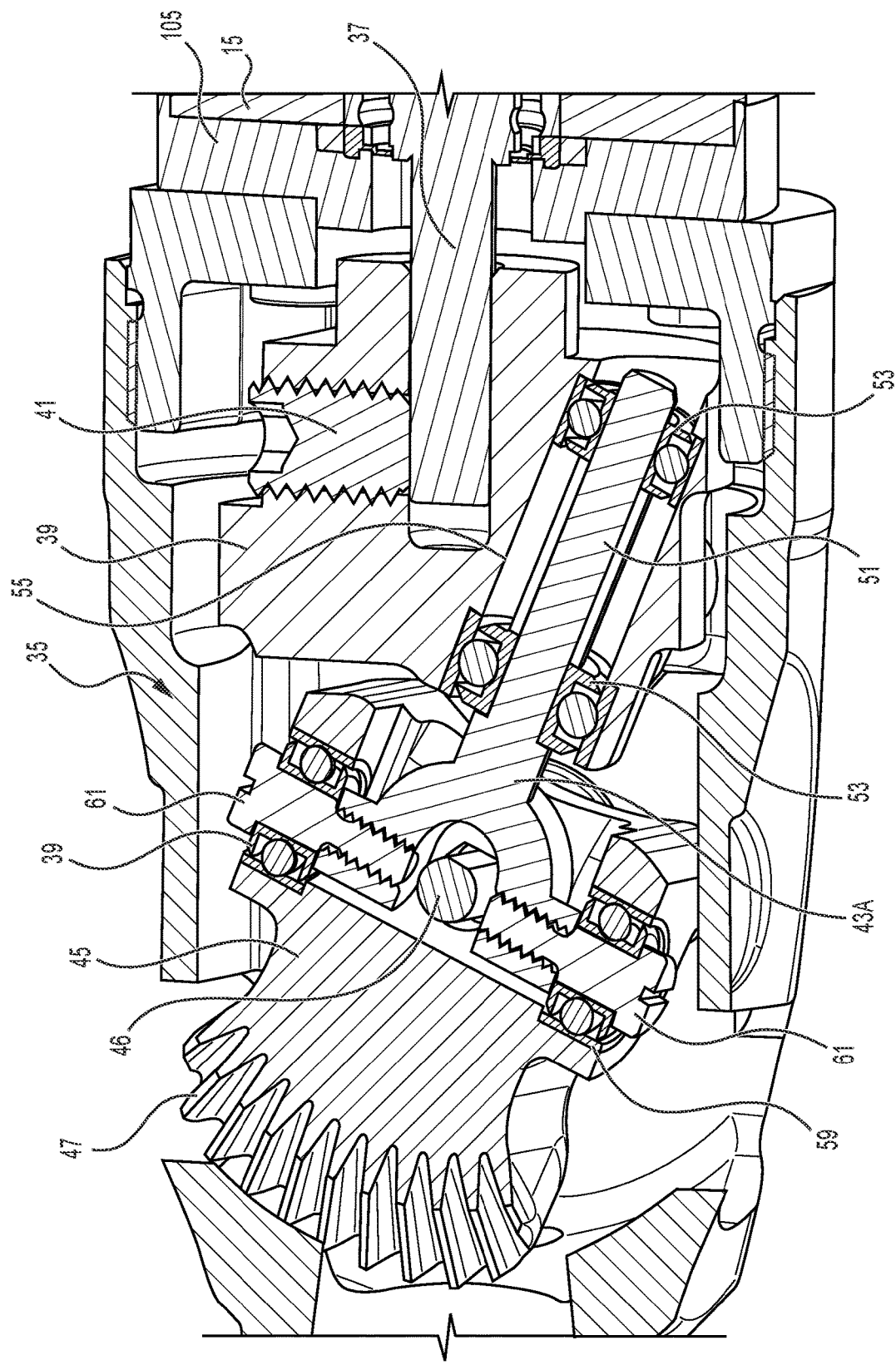
FIG. 2 is an isometric view of a portion of a first drive mechanism usable to effect oscillating rotation of an end effector.

FIGS. 2-5 illustrate four forms of couplers between the motor 15 and the oscillating rotation drive mechanism 35 described below. The drive mechanism 35 is coupled to the shaft 37 of the motor 15, as with a crank assembly hub 39 suitably mounted to the shaft 37, as with a set screw 41. The drive mechanism 35 also includes a link 43A that revolves about the shaft 37 and is attached to a rotatably mounted shuttle 45. The shuttle 45 includes an arcuate rack gear 47 that, through oscillating rotation of the shuttle, effects reciprocating motion of the gear 47. As shown, the shuttle 45 is rotatably mounted in the housing 13 via a shaft 46 secured to the shuttle 45, as on bearings 49 that are mounted in the housing 11, see FIG. 7. The difference between the four versions of drive mechanisms shown in FIGS. 2-5 is how the link 43 is attached to the shuttle 45. As seen in FIG. 2, the link 43A includes a shaft portion 51 that is both rotationally and reciprocally mounted to the hub 39 as being slidably mounted in bearings 53 that are mounted in a bore 55 that is positioned at an acute angle relative to the longitudinal axis of the output shaft 37 of the motor 15. While ball bearings 53 are shown, any suitable bearing(s) can be used, such as a sleeve bearing. The link 43A is attached to the shuttle 45 as by being rotationally mounted to bearings 59 mounted in the shuttle 45 as with fasteners 61. Rotation of the rotor of the motor 15 thereby effects oscillating movement of the gear segment 47 about the shaft 46.

Figure 3:
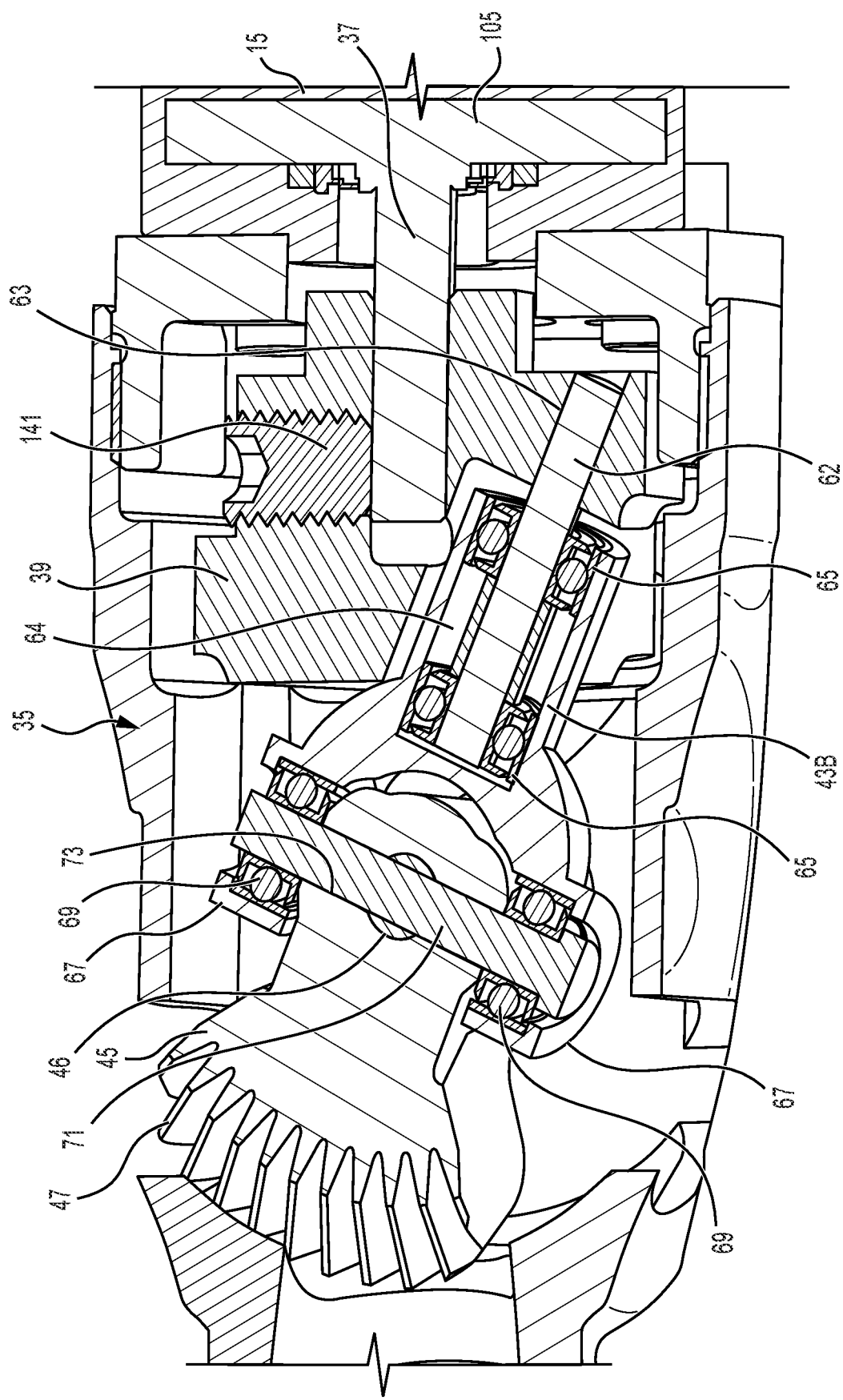
FIG. 3 is an isometric view of a portion of a second drive mechanism usable to effect oscillating rotation of an end effector.

FIG. 3 illustrates a second form of coupling of the crank assembly hub 39 to the shuttle 45. In this embodiment, a shaft 62 is mounted to the hub 39 and has a portion extending into a bore 63 in the hub 39. The link 43B has a bore 64 that has one or more bearings 65 mounted therein, with the shaft 62 being rotatably and reciprocally mounted in the bearing(s) 65 and preferably fixed to the hub 39. The link 43B is attached to the shuttle 45, as by having a pair of spaced apart arms 67 each having a bearing 69 which receives therein a shaft 71 that is rotatably received within the bearings 69 and is mounted in the shuttle 45 in a bore 73. Rotation of the hub 39 effects oscillating movement of the gear 47.

Figure 4:
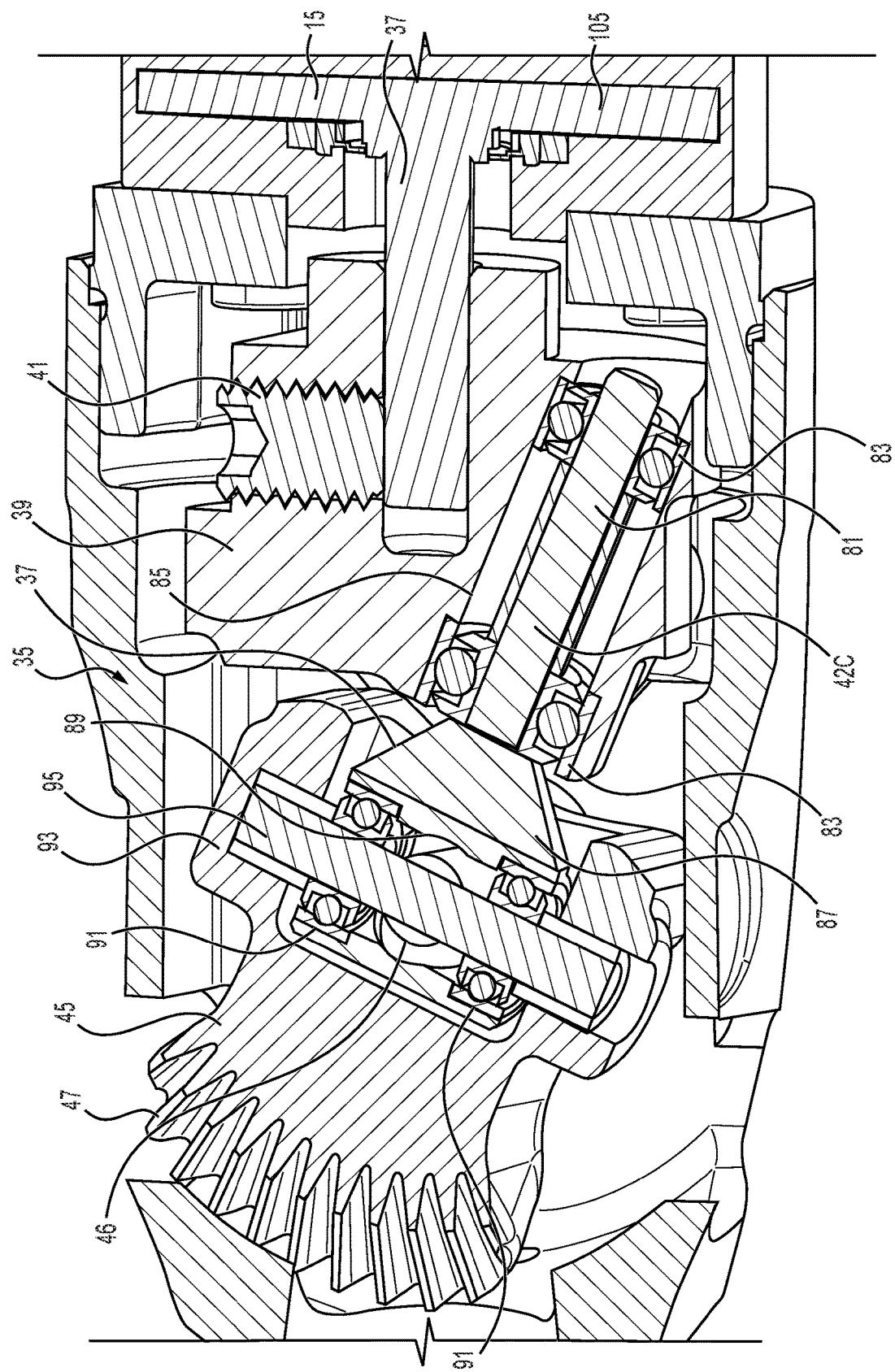
FIG. 4 is an isometric view of a portion of a third drive mechanism usable to effect oscillating rotation of an end effector.

FIG. 4 illustrates a third form of coupling of the motor 15 to the shuttle 45. The link 43C includes a shaft portion 81 that is rotatably and reciprocally mounted in a pair of bearings 83 that are in turn mounted in a bore 85 in the hub 39. As shown, the link 43C has a head portion 87 fixed to the shaft portion 81, and has a through bore 89 in which a pair of bearings 91 are mounted. The shuttle 45 has a bore 93, which is shown closed at one end, in which a pivot shaft 95 is mounted. The shaft 95 is rotatably mounted in the bearings 91 and attaches the link 43C to the shuttle 45. As shown, the head portion 87 is received within a cavity 97 in the shuttle 45 with sufficient room to effect relative movement between the head portion 87 and the shuttle 45. Rotation of the hub 39 effects oscillating movement of the gear 47.

Figure 5:
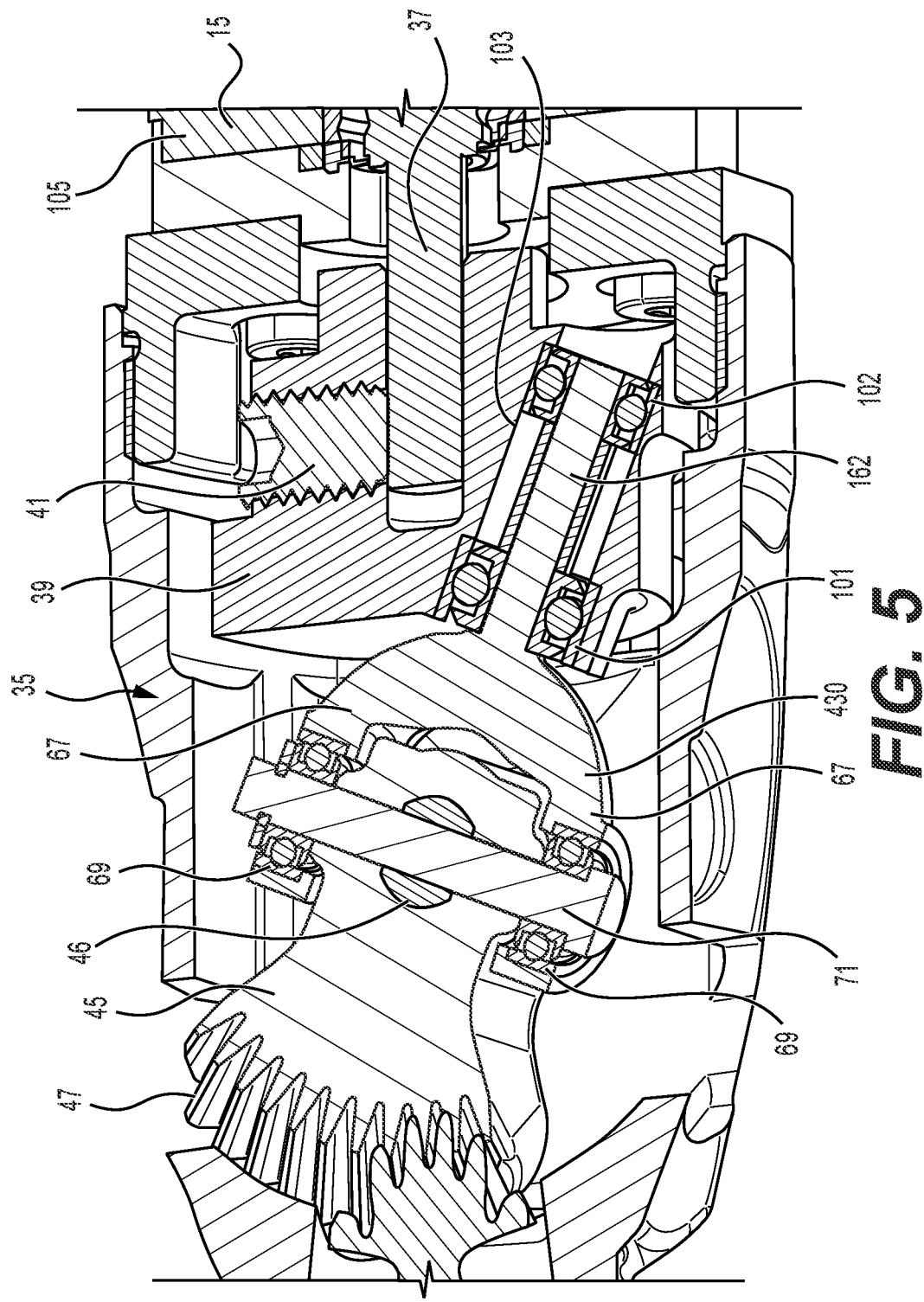
FIG. 5 is an isometric view of a portion of a fourth drive mechanism usable to effect oscillating rotation of an end effector.

FIG. 5 illustrates a fourth form of connection of the motor 15 to the shuttle 45. It is similar to the form of connection shown in FIG. 3, except for the mounting of a shaft to the hub 39. The shuttle 45 is attached to the link 43D via a shaft 71 mounted in the bearings 69, which in turn are mounted to respective arms 67. The link 43D includes a shaft portion 101, which in turn is slidably and rotatably mounted in bearings 102, which are in turn mounted in a bore 103. Rotation of the hub 39 effects oscillating movement of the gear 47.

In operation, rotation of the hub 39 by rotation of a rotor 105 of the motor 15 effects reciprocating rotation of the shuttle 45 and the gear segment 47 for a purpose described below. In one embodiment, the motor 15 can be a reversible motor, wherein direction of rotation can be selected by a switch 31 (for a purpose later described) when the tool 11 is in fastener driving mode.

Figure 6:
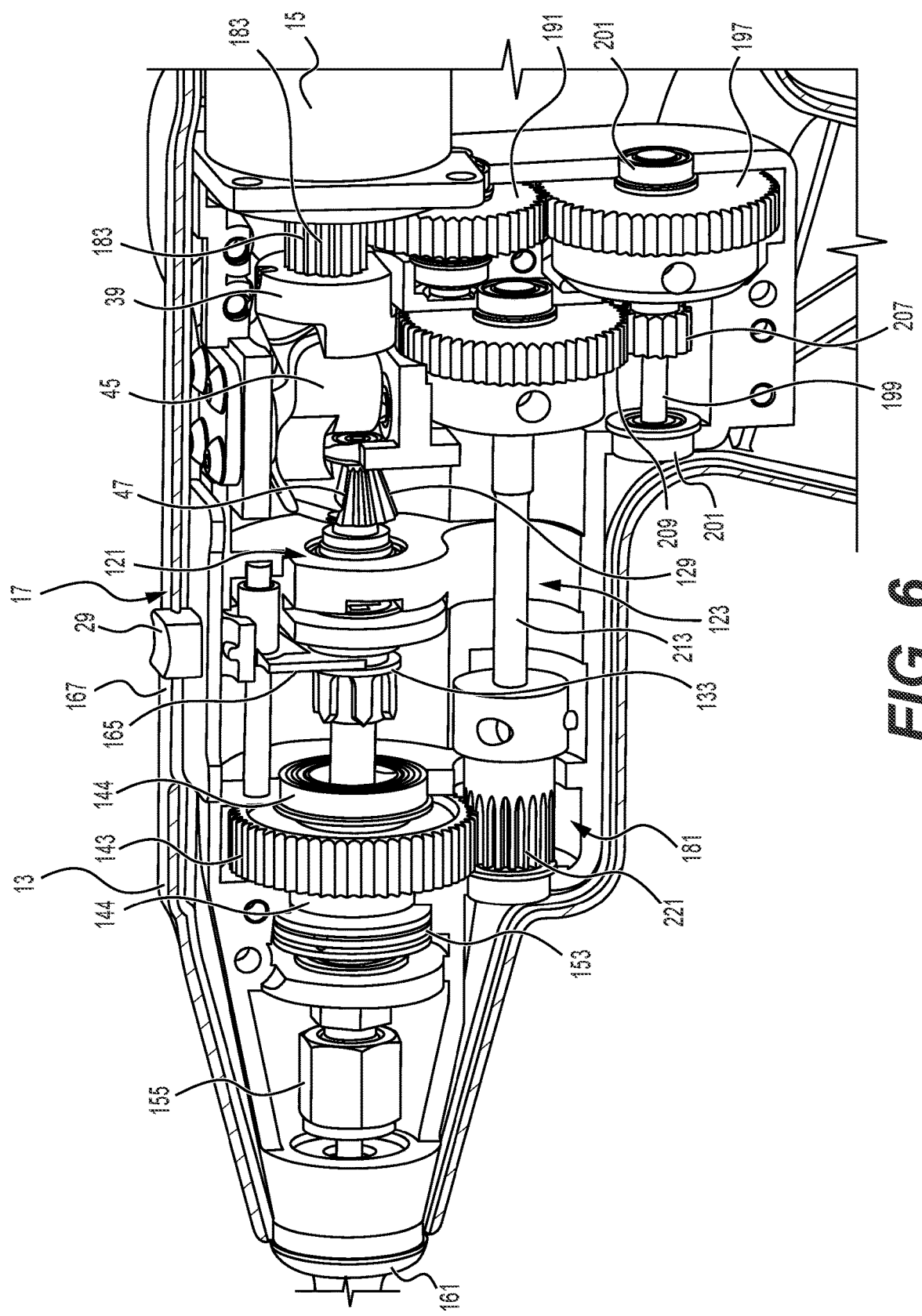
FIG. 6 is a fragmentary isometric view of a transmission usable to effect alternately oscillating and non-oscillating rotation of an output shaft shown configured to effect oscillating rotation of an output shaft.
Figure 7:
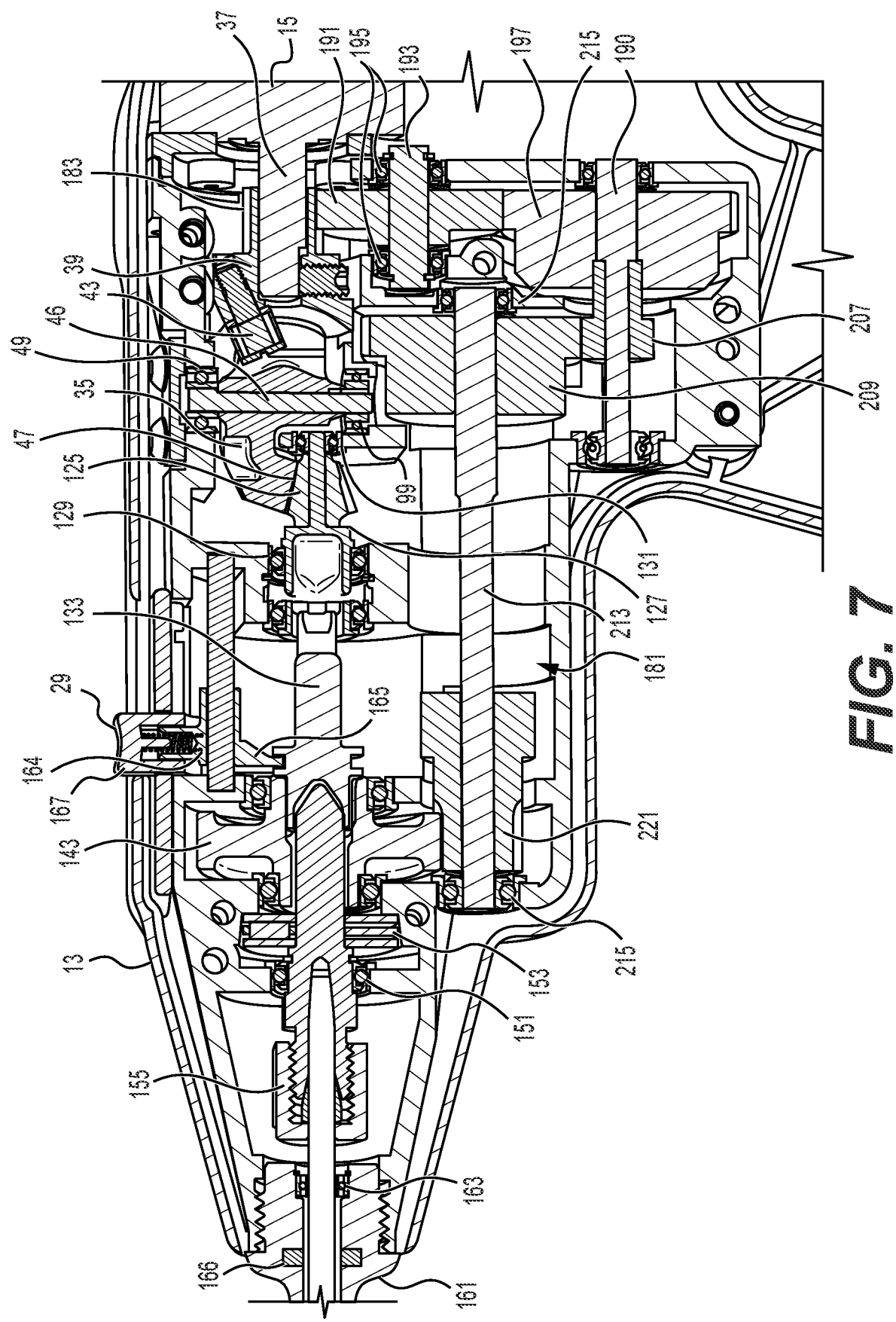
FIG. 7 is a fragmentary side elevation view of the transmission of FIG. 6 shown configured to effect non-oscillating rotation of an output shaft.

FIGS. 1, 6 and 7 illustrate further details of the transmission 17, which is operable to effect the oscillating rotational driving of the output shaft 19 at high speeds, such as 10,000 orbits per minute or higher, and selectively alternate a slow speed rotational driving of the output shaft 19 for the insertion or removal of a fastener into a surgical site. The above described drive mechanisms 35 effect oscillating rotational driving of the output shaft 19.

Figure 9:
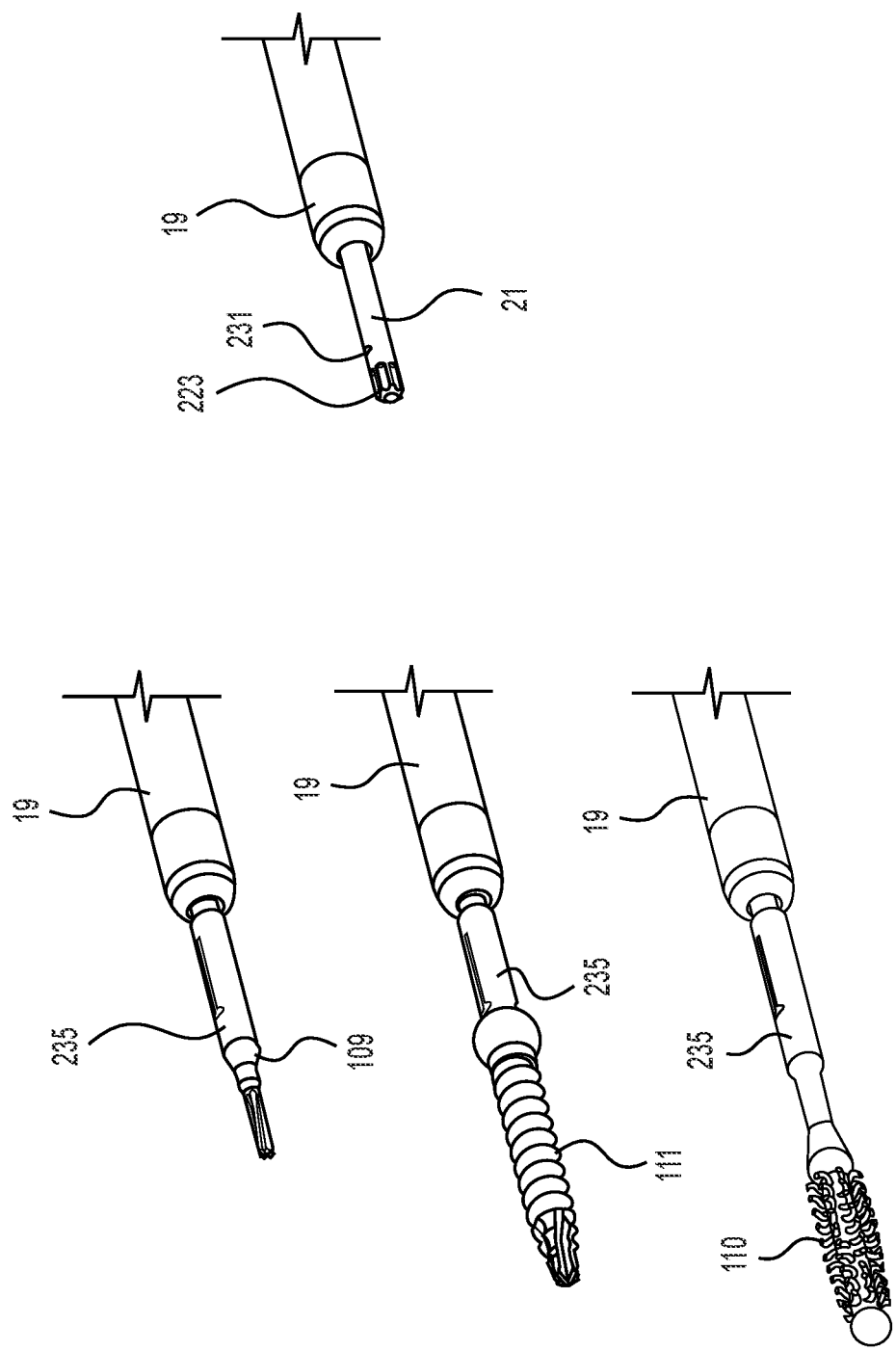
FIG. 9 is an isometric view of the three forms of end effectors.

The transmission 17 is constructed to selectively convert rotation of the shaft 37 of the motor 15 rotor 105 into oscillating rotation of the output shaft 19 for tissue modification, as with a cutting tool 109, 110, or continuous rotation of the output shaft 19 for the driving of a fastener (such as a screw) 111 into a patient's skeletal element, such as a vertebra, see FIG. 9. As best seen in FIG. 6, the transmission 17 includes a plurality of drive components, with at least one component, designated generally 121, being operable to effect oscillating rotation of the output shaft 19 for tissue modification; and another component, designated generally 123, being operable to effect continuous rotation of the output shaft 19 for driving a fastener 111.

Figure 8:
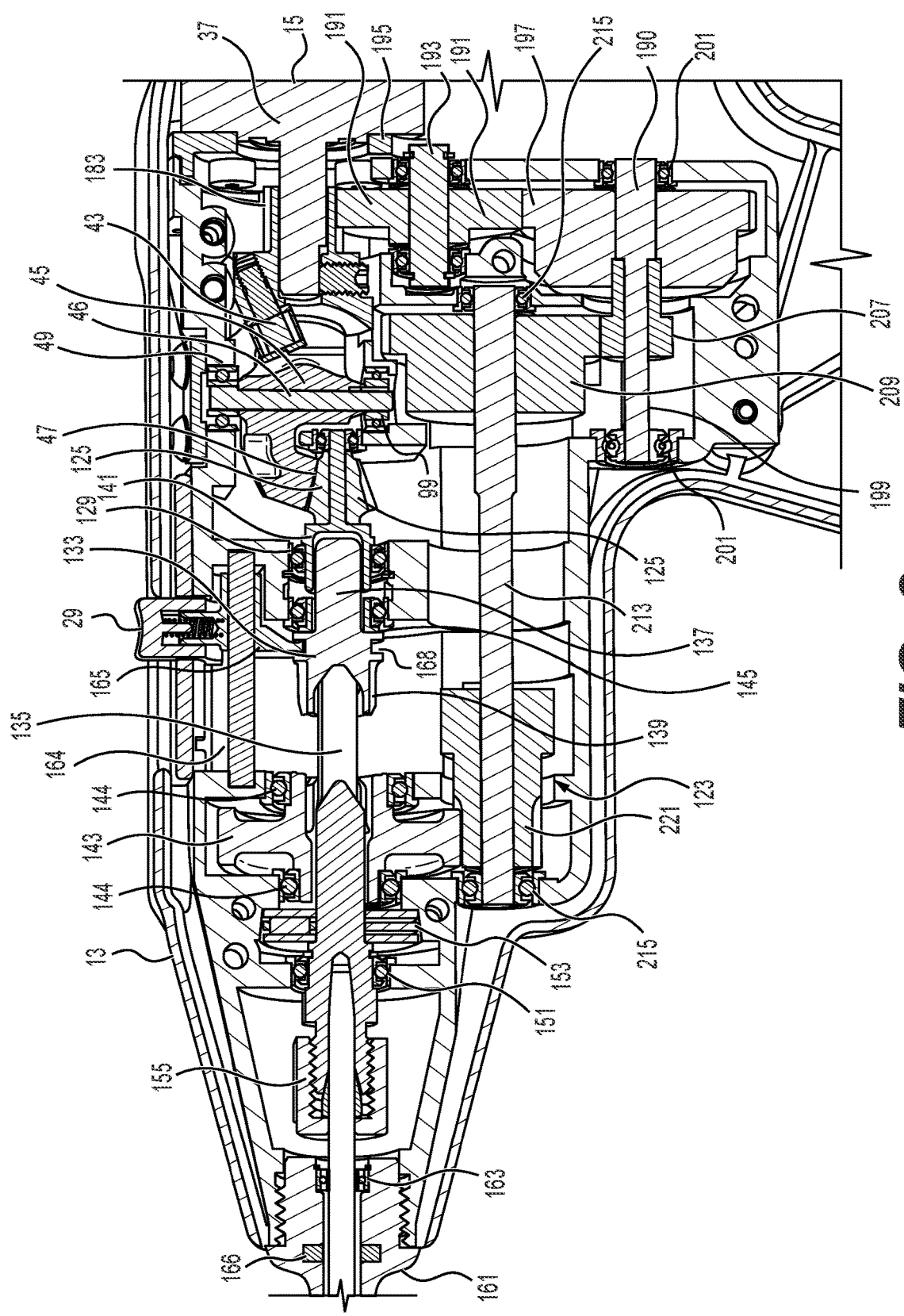
FIG. 8 is a fragmentary side elevation view of the transmission of FIG. 6 shown configured to effect oscillating rotation of an output shaft.

A gear 125, such as a bevel gear, meshes with the gear segment 47, whereby oscillating motion of the gear segment 47, induced by rotation of the hub 39, is mounted to a shaft 127 that is rotatably mounted in the housing 13, as with bearings 129, 131. A selector shuttle 133 is reciprocally slidably mounted on an axle 135 in a manner to permit relative sliding movement of the shuttle 133 on the axle 135 and prevent relative rotation therebetween. The shuttle 133 has opposite end portions 137, 139 that are each adapted to drivingly engage a bevel gear hub 141 or an output gear 143 to select between oscillating rotation of the output shaft 19 or continuous driving of the output shaft 19. In a preferred embodiment, the end portion 137 can be splined, as can the interior portion of the bevel gear hub 141, to selectively prevent relative rotation when engaged. The gear 143 is rotatably mounted in the housing 13 as by bearings 144. The shuttle 133 is rotatably and longitudinally slidably carried in the housing 13 by a bearing 145 mounted in the housing 13. FIGS. 6, 8 illustrate the shuttle 133 in a position to effect oscillating rotation of the output shaft 19; and FIG. 7 illustrates the shuttle 133 in a position to effect driving rotation of the output shaft 19. The axle 135 is rotatably mounted in a forward bearing 151 mounted in the housing 13 and is limited in longitudinal movement by being mounted in a thrust bearing 153 secured within the housing 19. The axle 135 is coupled to the output shaft 19 in any suitable manner and, as shown, is coupled using a threaded compression fitting 155. The proximal end of the output shaft 19 is mounted to the housing 13, as for example, by a threaded nose fitting 161 that has a bearing 163 mounted therein for supporting the output shaft 19 and providing support for the forward end of the axle 135. The threaded nose fitting 161 can be provided with a seal 166 about the output shaft 19 if desired.

Movement of the selector shuttle 133, as shown, is effected by a selector device 167, such as a slidably mounted actuator mounted to the housing 13. The selector device 167 can be movably mounted on a slide 164 suitably secured within the housing 13. The selector device 167 includes a fork 165 received within an annular groove 168 that allows the fork 165 to effect forward and aft movement of the shuttle 133 on the axle 135, while allowing rotation of the shuttle 133 during rotation thereof.

The transmission 17 is provided with structure to effect a second mode of selective operation: continuous rotation of the output shaft 19. In addition to the drive elements described above that effect oscillating rotation of the output shaft 19, the transmission 17 is operable to selectively effect the continuous rotation of the output shaft 19 to, for example, drive a screw or other type of fastener 111. This portion of the transmission 17 is best seen in FIGS. 1, 6, 7, 8. This portion of the transmission 17 is designated generally 123, and includes various combinations of gears, described below, to effect the desired gear reduction to provide the desired output rotation speed of the output shaft 19 given a motor 105 rotation speed. The below described gears can be spur gears, helical gears, other suitable gears, and combinations thereof.

As shown, the hub 39 can be provided with a gear portion 183 which will rotate when the shaft 37 of the motor 15 has its rotor 105 rotating. It is noted here that the motor 15 can be an electric motor or a compressed air operated motor, with an electric motor being preferred. The motor 15 is operably connected to a source of electricity via a power cord 23, with the switch 31 being operable to selectively effect operation of the motor 15. In the illustrated structure, the gear portion 183 meshes with a first gear 191 that is mounted on a shaft 193 that is in turn rotatably mounted in the housing 13 via a pair of bearings 195. The gear 191 is in driving engagement with a second gear 197 that is rotatably mounted in the housing 13 via a shaft 199 rotatably carried by the housing 13 via a pair of bearings 201. In turn, the gear 197 is coupled to an output gear 207, which is fixed to the gear 197 in a manner to effect simultaneous rotation therewith. The gear 207 is in turn drivingly engaged with a gear 209, which is rotatably mounted in the housing 13 via a shaft 213, which is rotatably mounted in the housing 13 by a pair of bearings 215. A gear 221 is also mounted on the shaft 213 to rotate with the gear 209 and meshes with gear 143. When the selector device 167 is moved to a forward position in the illustrated structure (FIG. 7), the gear 143 is drivingly coupled to the shaft 135, while the gear 125 is decoupled from the driving engagement with the axle 135, whereby the axle 135 is now being driven by the gear 143 along with the gears 191, 197, 209 and 221. The gear ratio of this gear train is such as to provide the desired output rotational speed of the output shaft 19 by the motor 15. If desired, the direction of rotation of the motor 15 can be reversed using switch 31 to provide either fastener insertion or fastener extraction.

FIG. 9 shows the distal end portion of the output shaft 19. It includes the tool coupler 21 that is operable for removably mounting different end effectors to the output shaft 19 and preventing relative rotation between the end effectors and the output shaft 19 during rotation, either continuous or oscillating rotation. As shown, an end effector 109 is operable for removing hard tissue, such as bone, and can be mounted on the coupler 21. Also as shown, a fastener 111 can be removably mounted to the coupler 21, wherein the output shaft 19 is operable to effect insertion (or removal) of the fastener 111 into a portion of the surgical site, such as a vertebra. Also shown, a soft tissue removal end effector 110 can be removably mounted to the coupler 21. The end effectors 109, 110 and 111 can be removably mounted to the coupler 21 and held in place by a ball and detent arrangement 231, as is known in the art. As also known in the art, relative rotation can be prevented between the coupler 21 and one of the end effectors 109, 110, 111 as by having a spline portion 233 engageable with a corresponding spline portion (not shown) inside a shank portion 235 of the end effectors 109, 110, 111.

Figure 10:
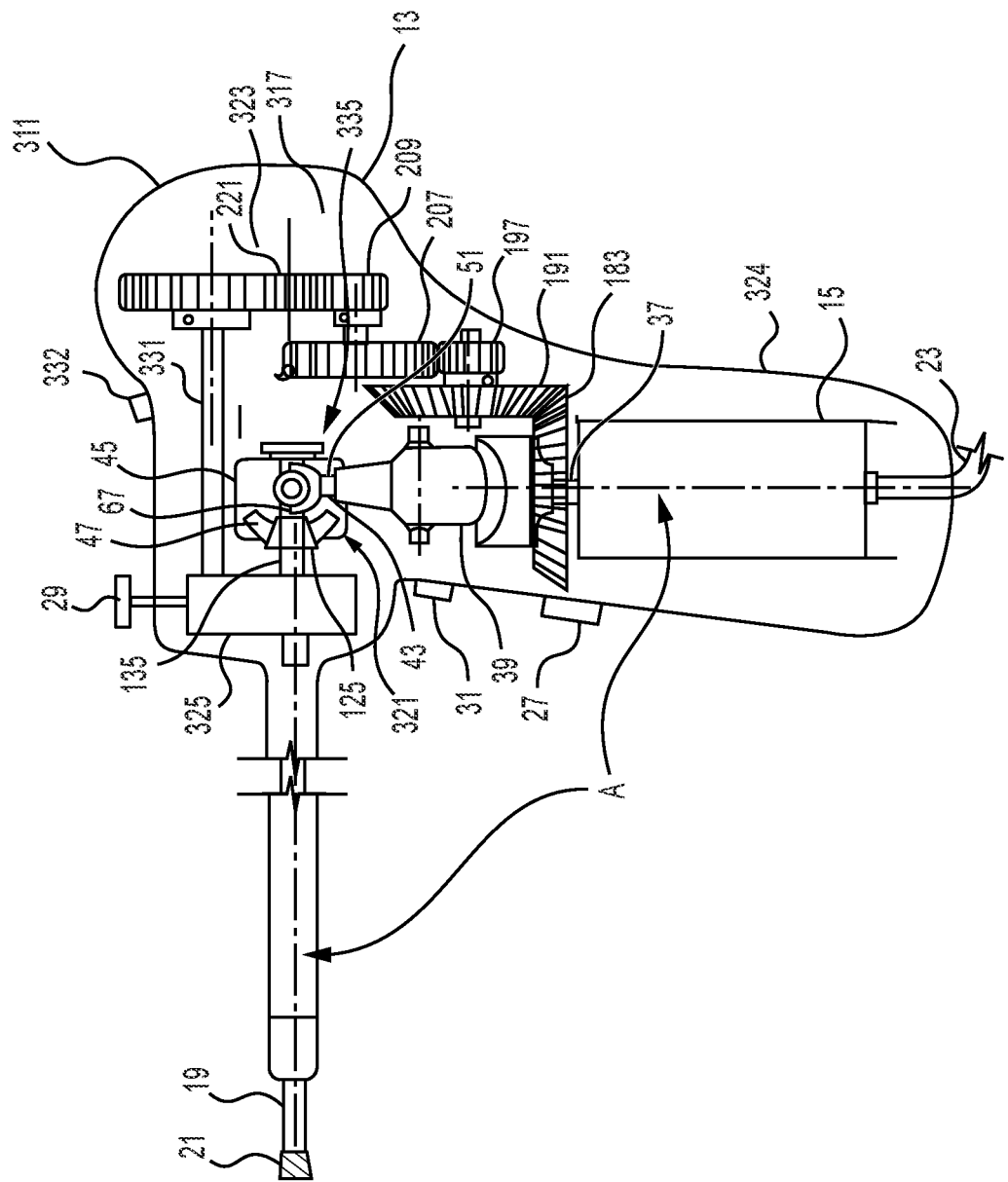
FIG. 10 is a fragmentary side view of a second form of a surgical tool showing internal drive components; some components are shown schematically.

FIG. 10 shows a second form of the above described invention. The principal difference between the above described surgical tool 11 and the surgical tool 311 illustrated in FIG. 10 is the orientation of the motor 15 and its output shaft 37 relative to the orientation of the output shaft 19 described above. As shown, the axis of rotation of the motor 15 in this second form is at an approximate right angle A to the axis of rotation of the output shaft 19. Preferably, the angle A is between about 80° and about 120°. The surgical tool 311 includes an on-off switch 27 and a motor reversing switch 31 for controlling operation of the motor 15 to which they are operatively connected. The motor 15 can be connected to an electrical power source as with a power cord 23. A tool coupler 21 is operably associated with the output shaft 19 as described above. Like numbers are used for the components in the surgical tool 11 and surgical tool 311 when the parts are similar in construction and operation to the first form of the invention shown in FIGS. 1-9.

The surgical tool 311 includes a transmission 317 that includes two drive components 321 and 323. The drive component 321 includes an oscillating drive mechanism 335 similar to the oscillating drive mechanism 35 described above. The drive components 321 and 323 are similar in construction and operation to the drive components 121 and 123 described above, respectively. The transmission 317 is mounted in a housing 13. The housing 13 includes a handle portion 324 that is positioned at a generally right angle A relative to the axis of rotation of the shaft 19.

The drive component 321 is similar in construction and operation to the drive component 121. It includes a crank assembly hub 39 as described above. The shuttle 45 is operably connected to the crank assembly hub 39, for example as shown in FIGS. 2-5 and particularly FIG. 3, utilizing a shaft 62 and a pair of arms 67. A gear 125, such as a bevel gear, engages the rack 47. As shown in FIG. 10, the rack 47 is at a rotational position about its axis of rotation relative to the axis of rotation of the shaft 37 of the motor 15 of the angle A relative to the rotational position of the rack 47 shown in FIGS. 1-9. The gear 125 is mounted on the axle 135 to effect its oscillating rotations and, in turn, oscillating rotation of the shaft 19. A selector mechanism, shown schematically as 325, has a selector transmission operation mode selector 29, as described above. The selector mechanism 325 includes a selector shuttle 133 mounted on the axle 135 and selectively positionable to drive an output gear 143; all not shown in FIG. 10, but are shown in FIGS. 1-9.

The second drive component 323 includes a series of gears, such as those described and shown in FIG. 6. An output gear 183 is mounted to the output shaft of the motor 15 and is operable to drive a series of gears discussed above. As shown, the gear 183 is shown as a bevel gear, and the gear 191 is shown as a corresponding bevel gear, such that the axes of rotation of the various gears in the second drive component 323 are at right angles to the axis of rotation of the motor 15. These gears include gears, such as gears 197, 207, 209 and 221. The gear 221 drives a shaft 331, which in turn will drive a gear (not shown) in the selector mechanism 325, which in turn will drive the shaft 19 when the selector shuttle 133 is moved by the mode selector 29, as described above. It is to be noted that a clutch (not shown) can be associated between the output shaft 37 of the motor 15 to selectively engage driving of the gear 183. Such a clutch can be electrically operated and can be provided with a control switch 332.

Thus, the tool 311 can be driven in an oscillating rotation manner using the rack 47 and gear 125, or can be driven in a continuous rotational manner using the drive component 323. The continuous rotation can be reversed by, for example, the use of a switch 31 which can reverse the direction of rotation of the motor 15.

Figure 11:
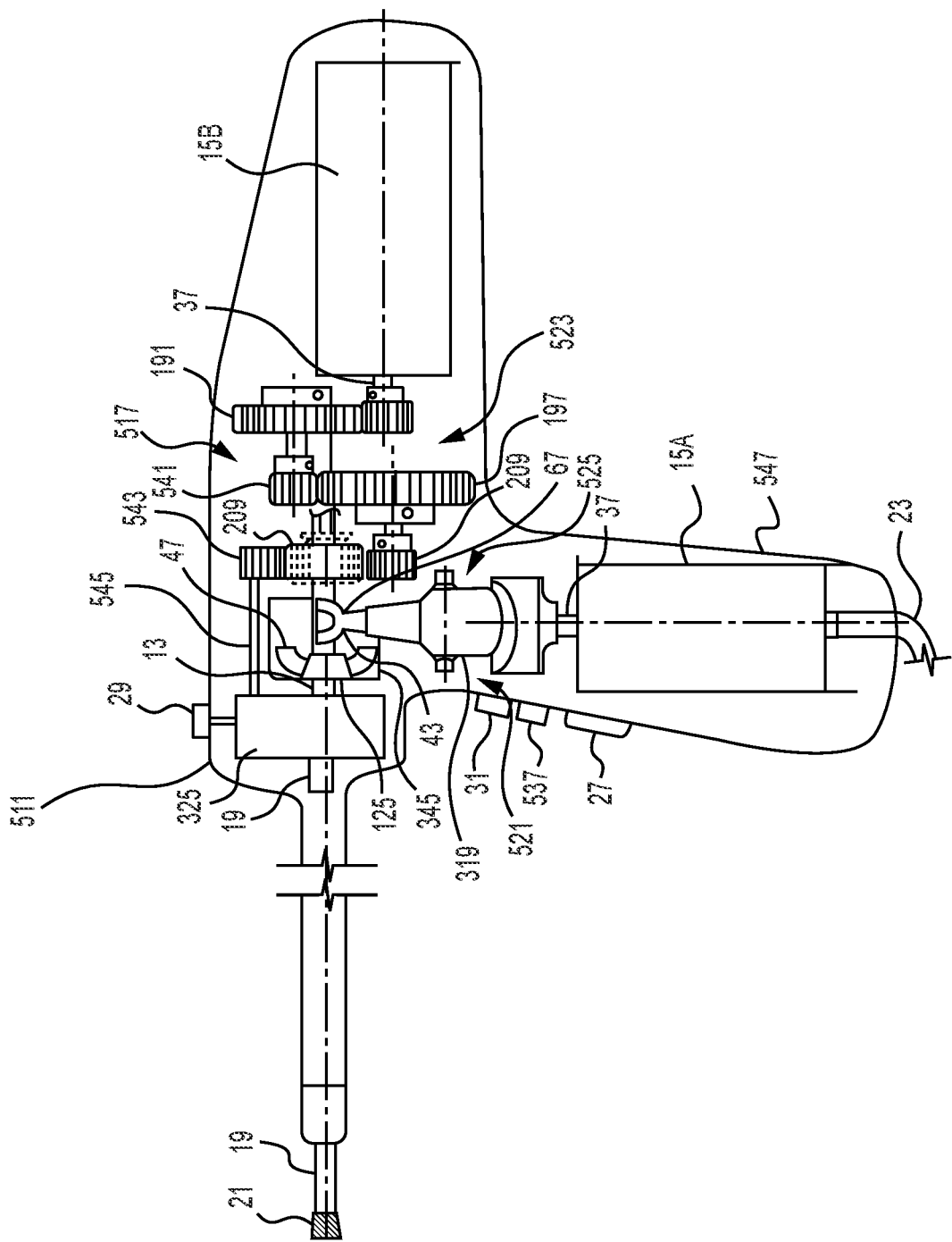
FIG. 11 is a fragmentary side view of a third form of a surgical tool showing internal drive components, some components are shown schematically.

FIG. 11 illustrates a third form of the present invention. This surgical tool is designated generally 511, and utilizes a pair of motors designated generally 15A, 15B instead of a single motor 15 as shown for the first and second forms of the surgical tools described above. Like the second form of the invention, the surgical tool 511 includes a transmission 517 that includes a pair of drive components 521, 523 similar in function and construction to the drive components 321, 323, respectively. The transmission 517 also includes an oscillating drive mechanism 535 similar to the oscillating drive mechanism 35 described above. The motor 15A operates the drive component 521 which includes a hub 319, a shuttle 45, a rack 47, a gear 125 and an axle 135 as described above for the second form of the invention illustrated in FIG. 10. The motor 15A can be controlled by the switches 27, 31, as described above. The form of the invention shown in FIG. 11 utilizes a selector mechanism 325, also as described above, that utilizes an operation mode selector 29 to determine if the output shaft 19 is to be driven in an oscillating manner or a continuous rotational manner. The surgical tool 511 includes a housing 13. It also includes an output shaft 19 and a tool coupler 21.

In this third form of the invention, a second motor 15B is provided and is operably associated with the drive component 523 for effecting its operation of continuous rotation of the shaft 19. The second motor 15B can be operated by the switches 27, 31. A third switch 537 is provided to select whether motor 15A or 15B is to be operated, and the reversing switch 31 is utilized to determine the direction of rotation of the motor 15B. The motor 15B is operably connected to the drive component 523 via its output shaft 37. A series of gears, such as those shown in the first invention embodiment as seen in FIG. 6, includes a gear 183 that meshes with a gear 191 as through an intermediate gear 541. Further driving is effected through a series of operably associated gears 207, 209 and 543. The gearing arrangement in the second drive component 523 is to effect a desired gearing ratio to drive an output shaft 545 that is operably connected to an output gear 221, seen in FIG. 6 and which is not shown in FIG. 11. A selector mechanism, shown schematically as 325, described above, has a selector transmission operation mode selector 29, as described above. The selector mechanism 325 includes a selector shuttle 133 mounted on the axle 135 and selectively positionable to drive an output gear 143, all not shown in FIG. 11, but shown in FIGS. 1-9. The output gear 143 is operably associated with the shaft 545 to selectively effect its driving.

In operation, the user of the surgical tool 511 grips the handle 547 and through a selection operation with the operating mode selector 29 and with switch 537, the user can select whether the output shaft 19 will drive in an oscillating manner or in a continuous rotation manner by selecting which motor, 15A or 15B, will operate. After selecting the operating mode, if oscillating driving of the shaft 19 is to be used, then the user can simply activate the switch 27 to operate motor 15A. If the operating mode is for continuous rotation of the shaft 19, then the user would also select the direction of rotation using the switch 31. In both operating modes, the operation mode selector 29 is placed in the appropriate position for selecting oscillating rotation or continuous rotation of the shaft 19.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while certain forms of the invention are illustrated, it is not to be limited to the specific forms or arrangements herein described and shown. It will be apparent to those skilled in the art that various changes may be made without departing from the scope of the invention, and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures, and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. An oscillating drive mechanism for a surgical tool comprising:
   a motor, the motor having a rotor rotationally secured within the motor, an output shaft secured to the rotor to rotate therewith;
   a crank assembly hub secured to the output shaft to rotate with the rotor and shaft;
   a link secured to the crank assembly hub, a longitudinal axis of the link positioned at an acute angle relative to a longitudinal axis of the output shaft of the motor so that the longitudinal axis of the link and the output shaft of the motor intersect at a point beyond a distal end of the output shaft;
   a pivot shaft positioned at the intersection of the longitudinal axis of the output shaft of the motor and the longitudinal axis of the link, the pivot shaft being constructed and arranged to prevent rotation of the link around its longitudinal axis while allowing the longitudinal axis of the link to rotate around the longitudinal axis of the output shaft of the motor during rotation of the crank assembly hub;
   a shuttle including an arcuate rack gear secured to the link so that rotation of the crank assembly hub provides reciprocating rotary motion to the arcuate rack gear about the pivot shaft;
   a gear meshed with the arcuate rack gear, the gear secured to an output shaft;
   wherein rotational motion of the motor induces rotary oscillating motion to the output shaft.

2. The oscillating drive mechanism for a surgical tool as claimed in claim 1 wherein the crank assembly hub includes at least one bearing for rotationally supporting the link.

3. The oscillating drive mechanism for a surgical tool as claimed in claim 2 wherein the crank assembly hub includes a bore, the bore extending along the longitudinal axis of the link and sized to cooperate with an outer diameter of the at least one bearing, the link including a shaft portion sized to cooperate with an inner bore of the at least one bearing.

4. The oscillating drive mechanism for a surgical tool as claimed in claim 3 wherein the bore has sufficient depth to cooperate with two bearings, the shaft portion of the link having sufficient length to extend through the bore of the two bearings.

5. The oscillating drive mechanism for a surgical tool as claimed in claim 2 wherein the crank assembly hub includes a bore, the bore extending along the longitudinal axis of the link, a shaft portion secured to the link within the bore, the shaft portion sized to cooperate with an inner bore of the at least one bearing, the link including a link bore along its longitudinal axis, the link bore sized to cooperate with an outer diameter of the at least one bearing to support the link.

6. The oscillating drive mechanism for a surgical tool as claimed in claim 5 wherein the shaft portion has sufficient length to cooperate with two bearings, the link bore having sufficient length to cooperate with the two bearings to support the link.

7. The oscillating drive mechanism for a surgical tool as claimed in claim 1 wherein the pivot shaft is sized to cooperate with an inner bore of at least one bearing, an outer diameter of the at least one bearing in cooperation with the link.

8. The oscillating drive mechanism for a surgical tool as claimed in claim 1 wherein the link is attached to the shuttle by a pair of spaced apart arms each having an arm bearing which receives therein a shaft portion that is rotatably received within the arm bearings.

9. The oscillating drive mechanism for a surgical tool as claimed in claim 1 wherein the link has a head portion including a through bore in which a pair of bearings are mounted, the shuttle has a bore in which the pivot shaft is rotatably mounted in the bearings, and attaches the link to the shuttle.

10. The oscillating drive mechanism for a surgical tool as claimed in claim 1 including a transmission which operably couples the motor to the output shaft, the transmission including a plurality of drive mechanisms to provide two modes of operation, wherein in a first mode of operation, rotation of the hub by rotation of the rotor of the motor, effects reciprocating rotation of the shuttle and the arcuate gear rack to provide oscillating rotary movement of the output shaft, and operation of the transmission in a second mode provides continuous rotary motion to the output shaft.

11. The oscillating drive mechanism for a surgical tool as claimed in claim 10 wherein in the second mode of operation the transmission includes various combinations of gears constructed and arranged to provide a predetermined gear reduction to provide a desired output rotation speed of the output shaft given a predetermined rotor rotation speed.

12. The oscillating drive mechanism for a surgical tool as claimed in claim 11 wherein the hub is provided with a gear portion which will rotate when the output shaft of the motor has the rotor rotating, the gear portion meshes with a first gear that is mounted on a shaft that is in turn rotatably supported via a pair of bearings, a gear is in driving engagement with a second gear that is rotatably mounted via a shaft rotatably carried by a housing via a pair of bearings, the gear is coupled to an output gear, which is fixed to the gear in a manner to effect simultaneous rotation therewith, output gear is drivingly engaged with a gear which is rotatably mounted in the housing via a shaft, which is rotatably mounted in the housing by a pair of bearings, a gear is also mounted on the shaft to rotate with the gear, and meshes with a gear.

13. The oscillating drive mechanism for a surgical tool as claimed in claim 10 wherein the motor includes a switch for controlling the direction of rotation of the motor, the switch having a first position for clockwise rotation of the output shaft and a second position for counterclockwise rotation of the output shaft.

14. The oscillating drive mechanism for a surgical tool as claimed in claim 1 wherein the orientation of the motor and its output shaft is at an angle of between 80 and 120 degrees relative to the orientation of the output shaft.

15. The oscillating drive mechanism for a surgical tool as claimed in claim 1 wherein the orientation of the motor and its output shaft is at an angle of 90 degrees relative to the orientation of the output shaft.

\* \* \* \* \*